(12) United States Patent
Hernández Altamirano et al.

(10) Patent No.: US 9,074,123 B2
(45) Date of Patent: Jul. 7, 2015

(54) GEMINAL ZWITTERIONIC SURFACTANTS AS WETTABILITY MODIFIERS IN ENHANCED OIL RECOVERY PROCESSES

(75) Inventors: Raúl Hernández Altamirano, México City (MX); Luis Silvestre Zamudio Rivera, México City (MX); Violeta Yasmín Mena Cervantes, México City (MX); Hiram Isaac Beltrán Conde, México City (MX); Cecilia de los Ángeles Durán Valencia, México City (MX); Simón López Ramírez, México City (MX); Eduardo Buenrostro González, México City (MX); José Luis Mendoza De La Cruz, México City (MX); Jorge Alberto García Martínez, México City (MX); Erick Emanuel Luna Rojero, México City (MX); David Aarón Nieto Álvarez, México City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 132 days.

(21) Appl. No.: 13/884,925

(22) PCT Filed: Nov. 9, 2011

(86) PCT No.: PCT/MX2011/000134
§ 371 (c)(1),
(2), (4) Date: Jul. 23, 2013

(87) PCT Pub. No.: WO2012/064168
PCT Pub. Date: May 18, 2012

(65) Prior Publication Data
US 2013/0296200 A1 Nov. 7, 2013

(30) Foreign Application Priority Data

Nov. 12, 2010 (MX) .................. MX/a/2010/012348

(51) Int. Cl.
| | | |
|---|---|---|
| *C11D 1/62* | (2006.01) | |
| *C09K 8/584* | (2006.01) | |
| *C11D 1/06* | (2006.01) | |
| *C10G 1/04* | (2006.01) | |
| *C07C 229/12* | (2006.01) | |

(52) U.S. Cl.
CPC . *C09K 8/584* (2013.01); *C11D 1/06* (2013.01); *C10G 1/04* (2013.01); *C10G 2300/4006* (2013.01); *C10G 2300/44* (2013.01); *C07C 229/12* (2013.01)

(58) Field of Classification Search
CPC .................................. C09K 8/584; C11D 1/06
USPC .................................................. 510/407, 506
See application file for complete search history.

(56) References Cited

U.S. PATENT DOCUMENTS

| 6,034,271 | A | 3/2000 | Kwetkat |
| 8,518,868 | B2 * | 8/2013 | Hernandez Altamirano et al. ............... 510/479 |
| 2006/0024691 | A1 * | 2/2006 | Benz .................. 435/6 |
| 2009/0054368 | A1 | 2/2009 | Wettig et al. |
| 2011/0071056 | A1 | 3/2011 | Saini et al. |
| 2011/0138683 | A1 | 6/2011 | Hernandez Altamirano et al. |
| 2011/0269652 | A1 * | 11/2011 | Marangoni et al. ........... 507/240 |

OTHER PUBLICATIONS

International Search Report for PCT/MX2011/000134, dated Mar. 21, 2012.

* cited by examiner

*Primary Examiner* — John Hardee
(74) *Attorney, Agent, or Firm* — Roylance, Abrams, Berdo & Goodman, L.L.P.

(57) ABSTRACT

Geminal zwitterionic surfactants based on bis-N-alkyl, bis-N-alkenyl, N-cycloalkyl or N-aryl bis-beta amino acids or salts thereof as wettability modifiers of rocks such as limestone, dolomite, sand, quartz or heterogeneous lithologies.

33 Claims, 3 Drawing Sheets

GEMINAL ZWITTERIONIC SURFACTANTS AS WETTABILITY MODIFIERS IN ENHANCED OIL RECOVERY PROCESSES

FIELD OF THE INVENTION

This invention is related with the application of geminals zwitterionics liquids as wettability modifiers of rocks such as limestone, dolomite, sandstone, quartz or heterogeneous lithologies in the presence of brines with high content of divalent ions such as calcium, magnesium, barium and strontium, high temperature and high pressure in enhanced oil recovery process to increase oil recovery factor.

BACKGROUND OF THE INVENTION

Zwitterionics liquids are compounds that containing the cation and anion at different atoms of the same molecule, making them electrically neutral and gives them the opportunity to behave as acids or bases (donor or acceptor) depending on the characteristics of the medium which means they are intelligent molecules can be designed to work efficiently depending on the characteristics of one or more specific environmental.

Chemical structures of some zwitterionic liquids

Geminals zwitterionics liquids (2) are a family that is characterized by having two hydrocarbon chains (A), a molecular bridge (B), and two zwitterionic polar groups (C).

General structure of geminal zwitterionic liquid

For the particular case of the increase in oil production has to be after the primary and secondary recovery, the oil field still contains 50-80% of oil originally in place.

The efficiency of the methods of primary and secondary recovery is limited by two factors:

The scale of the pores, the crude oil can reach a sufficiently low residual saturation found as discontinuous cells, trapped by capillary forces.

The scale of the site, there are certain areas in which the fluid injected during secondary recovery does not penetrate, because of the low permeability of these zones.

Currently the proposed methods for the enhanced recovery involving one or more of these factors and the use of chemical products as wettability modifiers, is one of the most widely used, within which are cationic, anionic, nonionic and zwitterionic or mixture thereof.

Wettability modifier is defined as a surfactant capable of changing the affinity of reservoir rock in favorably manner. The wettability is a measure of the interaction between the phases present in the reservoir and is a function of interfacial chemistry of these phases and determines the tendency of a fluid for moving or adhering to a solid surface in the presence of other immiscible fluids. The wettability of a rock can be naturally modified by adsorption of polar compounds, the formation of deposits of organic material that was originally in the oil or by external agents. Changes in the wettability affect capillary pressure, relative permeability, residual oil saturation and irreducible water saturation. Additionally and equally important is the recognition that the confinement of the fluid substantially modifies the behavior of their phases with respect to its properties in the bulk.

Despite continued advances in the development of wettability modifiers, currently in Mexico there are reservoirs that very difficult to treat because they are naturally fractured, have low permeability, have lithologies heterogeneous, high temperatures (above 90° C.) and a high salinity usually greater than 60,000 ppm and a high content of divalent ions (calcium and magnesium, more than 5000 ppm).

Because of this, the characterization of the type of reservoir rock as well as the composition of adsorbed crude oil its of very important parameters for designing new wettability modifiers to propose molecular structures that are tolerable to salt saturated brine, mainly calcium and magnesium, good diffusion through the medium that is generally composed of brine, oil; and polar groups with affinity for the rock to change the wettability of oil-wet rock to wet by water.

Globally there are a variety of specific cases of chemicals that have been successfully used to solve these problems, within which are anionic surfactants such as sodium alkyl sulfonates or cationic surfactants like alkyl ammonium chlorides, but unfortunately your application is not universal, because the conditions are present in Mexican reservoirs are quite different from those, this is why that is very important the development of versatile chemicals products that can be used to increase the oil recovery at adverse conditions.

The following documents show some technologies to increase oil recovery:

U.S. Pat. No. 5,042,580 (Oil Recovery Process for use in fractured reservoirs) protects an enhanced oil recovery process that involves the injection in the reservoir a wettability modifier that consisting of a mixture of different types of surfactants like alkyl sulfonate type and chrome salts derived from fatty carboxylic acids.

U.S. Pat. No. 4,509,951 (Enhanced recovery by imbibition process) protects an enhanced recovery process that involves the injecting in the reservoir of a wettability modifier that consisting of a mixture of different types of products, within which are ammonium salts, hydroxides of alkalis metals, alkyl tripolyphosphates and carbonates and bicarbonates of alkali metals.

U.S. Patent Application 2009/0023618 A1 (Method of Oil Recovery) protects an enhanced recovery process that involves the injecting to the reservoir of a wettability modifier consisting of a mixture of different types of organophosphorus compounds.

U.S. Pat. No. 4,842,065 (Oil Recovery Process using a wettability modifying cyclic process) protects an enhanced recovery process that involves the injecting to the reservoir of wettability modifier that consisting of a mixture of different types of ethoxylates alcohols.

U.S. Pat. No. 3,643,738 (Control of wettability in oil recovery process), protect a process that it allows the change of wettability through the use of mixtures of petroleum sulfonates.

The present invention overcomes the above references cited notoriously under that geminals zwitterionics liquids bis-N-alkyl or N-alkenyl or N-cycloalkyl or N-aryl bis-beta aminoacids or its salts can be used as wettability modifiers of a variety of rocks such as limestone, dolomite, sandstone, quartz or heterogeneous lithologies, and may be exposed to high divalent ion such as calcium, magnesium, barium and strontium, temperatures up to 220° C. and pressures up to 300 kg/cm$^2$ in enhanced oil recovery process.

Therefore, the object of the present invention is the application of a composition based on geminals zwitterionics liquids in water with high content of divalent ions such as seawater or water from the reservoir or aromatic or hydrocarbon solvents with application as wettability modifiers for rocks such as limestone, dolomite, sandstone, quartz or heterogeneous lithologies in the presence of brines with high content of divalent ions such as calcium, magnesium, barium and strontium, high temperature and high pressure in enhanced oil recovery processes exposed to environments with a high content of divalent ions such as calcium, magnesium, barium and strontium and high temperature and high pressure to increase recovery oil factor Another object of the present invention is to provide an active compound based on geminal zwitterionic liquid bis-N-alkyl or N-alkenyl or N-cycloalkyl or N-aryl bis-beta aminoacids or its salts, such as wettability modifiers of oilfield rocks.

BRIEF DESCRIPTION OF THE DRAWINGS OF THE INVENTION

In order to gain a better understanding as to the application of geminal zwitterionic liquids as wettability modifiers of enhanced oil recovery process of the present invention, reference will be made to the accompanying figures.

DETAILED DESCRIPTION OF THE INVENTION

The present invention is related to the application of geminal zwitterionic liquids based on bis-N-alkyl or bis-N-alkenyl or N-cycloalkyl or N-aryl bis-beta aminoacids or its salts as wettability modifiers of rocks such as limestone, dolomite, sandstone, quartz or heterogeneous lithologies in environments that containing brines with a high content of divalent ions such as calcium and magnesium, high temperature and pressure. The composition comprises a geminal zwitterionic liquid bis-N-alkyl or N-alkenyl or N-cycloalkyl or N-aryl bis-beta aminoacids or its salts, using distilled water or brine with a high content of divalent ions such as calcium and magnesium or organic solvents derived from alcohols like methanol, ethanol, isopropanol or mixtures or aromatics such as xylenes, toluene, diesel, gasoline or blends as a solvents, this composition evaluated with a high content of divalent ions such as calcium, magnesium, barium and strontium, with a high temperature.

Geminal zwitterionic liquids with application as wettability modifiers object of the present invention is described below in the structure (3).

Structure 3. General structure of geminal zwitterionic liquids of the present invention Where:

$R_1$ is a radical represented by —H or —$CH_3$, $R_2$ is a alkyl or alkenyl chain, or an cycloalkyl or aryl group, $R_3$ is a radical represented by —H or —$CH_3$, n and m can have values from 1 to 250, depending on the molecular weight of polyether used, Zwitterionic liquids are obtained according to the procedure described below:

The reaction scheme of new gemini surfactants bis-N-alkyl polyether, bis-N-alkenyl polyether, bis-N-cycloalkyl polyether, bis-N-aryl polyether bis-beta or alpha-amino acids or their salts of structural formula VII, comprises three reaction steps:

1. The first step is to react polyalkyleneglycols of formula I, preferably derived from ethylene oxide and propylene oxide or copolymers of these having two hydroxyl groups, one at the end and the other at the beginning of the polymer chain whose molecular weight is in the range of 100 to 20,000 g/mol, with at least one of the compounds represented by the letter A: tosyl chloride, mesyl chloride, preferably tosyl chloride, where the reaction is carried out with a molar ratio of polyglycols of formula I and A compounds of 1:2 to 1:4, preferably 1:2.2 to 1:2.6, with alkaline sodium, potassium or cesium hydroxide, preferably sodium hydroxide, using water as a solvent, tetrahydrofuran or acetonitrile or mixtures thereof, a reaction time of 1 to 8 hours, preferably 3 to 5 hours at a temperature of 0 to 40° C., preferably from 10 to 30° C., to form compounds of Formula III; and 2. The second step consists of reacting the compounds of Formula III via nucleophilic substitution with compounds of Formula IV: linear or branched alkyl or alkenyl amines, preferably having 1 to 30 carbon atoms, or cycloalkyl or aryl, preferably having 5 to 12 carbon atoms, wherein the reaction is carried out with a molar ratio between the compounds of Formula III and IV of 1:1.5 to 1:4, preferably 1:1.8 to 1:2.6, in the presence of solvents such as acetonitrile, dimethylformamide, dimethylsulfoxide, acetone or short chain alcohols, preferably acetonitrile, at a reaction time of 1 to 10 hours, preferably 4 to 6 hours, and at a temperature of 60 to 100° C., preferably 70 to 85° C.; to obtain secondary amines of Formula V.

3. The third stage of reaction synthesis scheme is to obtain compounds of Formula VII: bis-N-alkyl polyether, bis-N-alkenyl polyether, bis-N-cycloalkyl polyether, bis-N-aryl polyether bis-beta or alpha-amino acids or their salts, which are obtained by reacting secondary amines of Formula V with compounds of Formula VI: unsaturated acids such as acrylic, methacrylic, itaconic, crotonic, fumaric, isocrotonic, angelic and maleic acids, among others, alpha or beta acids or halogenated as chloro-acetic acid, bromine-acetic acetic, bromine and chlorine propionic acids, or salts of the above acids, or unsaturated esters such as methyl acrylate and methyl methacrylate, among others, in which the reaction is carried out with respect molar among the compounds of Formula V and VI of 1:1.5 to 1:4, preferably 1:1.8 to 1:2.6. The reaction can be carried out in the absence or presence of solvents such as water, alcohols, aromatic hydrocarbon solvents or inert solvents, preferably water, toluene or xylene mixtures, o-xylene, m-xylene, p-xylene, kerosene and jet fuel. The reaction time, temperature and pressure depend on the structure of the compounds of Formula V and VI. Usually the reaction time varies from 1 to 24 hours, preferably 1 to 10 hours. The temperature ranges from 40 to 180° C., preferably 80 to 130° C., and the pressure is generally atmospheric, and can vary from 585 to 760 mmHg. The compounds of Formula VII can be neutralized with bases such as hydroxides, carbonates or bicarbonates of sodium, potassium or cesium.

Some practical examples for better understanding of the present invention, without limiting its scope, are discussed below.

EXAMPLES

Some practical examples for better understanding of the present invention, without limiting its scope, are discussed below.

Example 1

Preparation of 4,43-di(octadec-9-enyl)-7,10,13,16, 19,22,25,28,31,34,37,40-dodecaoxa-4,43-diaza-hexatetracontane-1,46-dioic acid. (Chemical product 1)

In a 500 ml balloon flask containing 59 g of an aqueous solution to 17 weight percent of sodium hydroxide (10 g) were added 50 g of polyethylene glycol whose number average molecular weight is 600 g/mol, the mixture stirred for 20 minutes. Then, at room temperature (25° C.) and atmospheric pressure (585 mmHg), very slowly 87 g of a solution of tosyl chloride at 40 weight percent (34.8 g) in tetrahydrofuran were added, keeping the temperature below 25° C. throughout the addition. After completion of addition, the reaction mixture was stirred for about an hour at room temperature and atmospheric pressure. Then the reaction mixture was made and extraction of organic phase and evaporated the solvent at reduced pressure, to obtain 74 g of Product A as a viscous clear yellow liquid with a yield of 98%.

As a second stage of reaction in a 500 ml balloon flask, equipped with a magnetic stirrer and a condenser were added 111 g of acetonitrile, 74 g of Product A, 43 g of oleylamine and 34 g of potassium carbonate. The reaction mixture was stirred vigorously at reflux temperature and atmospheric pressure for five hours, after which time the reaction mixture was filtered and the solution was evaporated to remove the solvent under reduced pressure. Finally the crude reaction product was evaporated to remove the solvent under reduced pressure. The crude reaction product was subjected to a solvent extraction and the organic phase was evaporated under reduced pressure, yielding 81 g of Product B as a clear liquid viscous yellow with a yield of 92%.

For the third reaction stage in a three-necked round bottom flask of 250 ml, equipped with a magnetic stirrer, a dropping funnel, a thermometer and a condenser were added 81 g of Product B at room temperature and atmospheric pressure and 10.6 g of acrylic acid were slowly added. The reaction mixture was stirred vigorously at a temperature not exceeding 100° C. and atmospheric pressure for 3 hours. It is noteworthy that the reaction is exothermic and it is important to keep the reaction below 100° C. When the reaction time was completed 89 g of the Product 1 were obtained as a very viscous clear yellow liquid, with a yield of 95%.

Example No. 2

Preparation of salt of 4,43-di(octadec-9-enyl)-7,10,13,16,19,22,25,28,31,34,37,40-dodecaoxa-4,43-diazahexatetracontane-1,46-dioic acid. (Chemical Product 2)

The chemical product 2 was obtained by neutralizing the chemical product 1 with 2 moles of sodium hydroxide.

Example No. 3

Preparation of 23,26,29,32,35,38,41,44-octamethyl-4,64-di((Z)-octadec-9-enyl)7,10,13,16,19,22,25,28,31,34,37,40,43,46,49,52,55,58,61-nonadecaoxa-4,64-diazaheptahexacontane-1,67-dioic acid. (Chemical product 3)

The chemical product 3 was obtained under the same scheme of chemical synthesis of product 1, for this product is used a copolymer derived from ethylene oxide and propylene oxide with an average molecular weight of 1000 g/mol and oleylamine.

Example No. 4

Determination of contact angle change. To simulate the conditions prevailing in an oil well, these conditions were established using a procedure for determining the contact angle rock/crude oil immersed in brine with a high content of divalent ions such as calcium and magnesium with additives and without additive, a temperature of 25° C.

Test Equipment and Apparatus.
 The devices consist of the following:
 Device for measuring the contact angle
  Quartz cell
Testing Procedures.
 1.—Using a rock cutting (limestone, dolomite, quartz) treated with the crude oil and introduced into the quartz cell.
 2.—Allow a drop of crude oil and measured the contact angle when the drop is stabilized.
 3.—Leave the drop at rest for 30 minutes.
 4.—Added a quantity of brine water feature sufficient training to fully immerse the rock.
 5.—After 2 hours dropped a crude oil droplets on the surface and measuring the contact angle.

The same procedure is followed for brines doped with the chemical composition of the present invention at various concentrations.

For this test were evaluated chemicals products 1, 2 and 3 at a concentration of 1000 ppm. Such structures are described below:

Where n = 12

4,43-di(octadec-9-enyl)-7,10,13,16,19,22,25,28,31,34,37,40-dodecaoxa-4,43-diazahexatetracontane-1,46-dioic acid (chemical product 1)

Where n = 12

Sodium salt of 4,43-di(octadec-9-enyl)-7,10,13,16,19,22,25,28,31,34,37,40-dodecaoxa-4,43-diazahexatetracontane-1,46-dioic acid (chemical product 2)

where n = 6 y m = 8

23,26,29,32,35,38,41,44-octamethyl-4,64-di((Z)-octadec-9-enyl)7,10,13,16,19,22,25,28,31,34,37,40,43,46,49,52,55,58,61-nonadecaoxa-4,64-diazaheptahexacontane-1,67-dioic acid (chemical product 3).

Two types of crude oil, whose characteristics are described in Tables 1 and 2. The brine used is described in Table 3.

Figure 1:
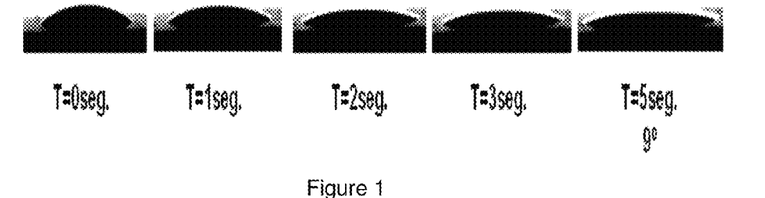
FIG. 1 shows the contact angle images of crude oil on dolomite without brine, and their behavior at different times.
Figure 2:
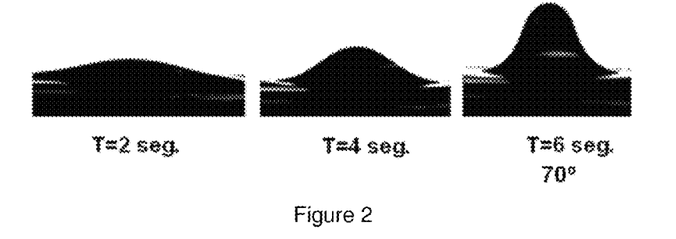
FIG. 2 illustrates the contact angle images of crude oil on dolomite with additive brine with chemical product 1 (4,43-di(octadeca-9-enyl)-7,10,13,16,19,22,25,28,31,34,37,40-dodecaoxa-4,43-diazahexatetracontane-1,46) dioic acid at a concentration of 1000 ppm at different contact times.
Figure 3:
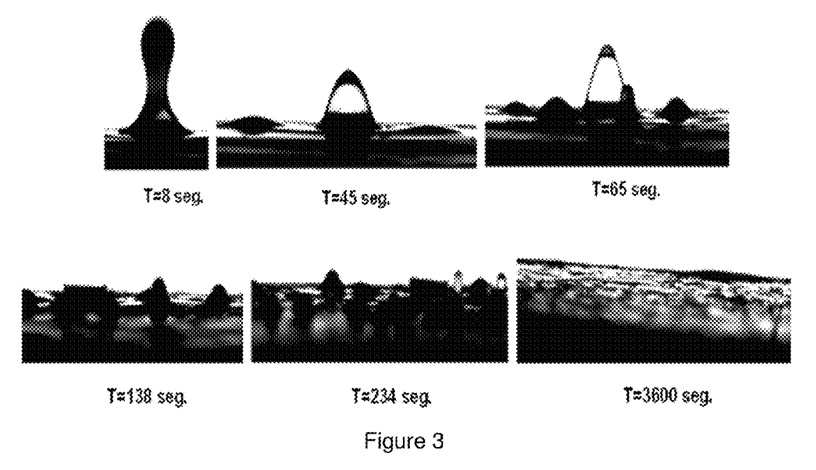
FIG. 3 is shown the images of the displacement of crude oil at different times of contact with the chemical product 1, at a concentration of 1000 ppm.
Figure 4:
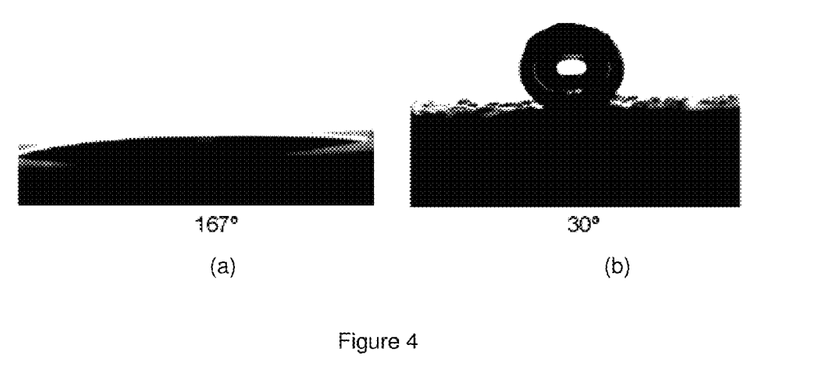
FIG. 4 shows the change in contact angle of a drop of crude oil A added after two hours of being immersed in brine without additive and with the chemical product 1 at a concentration of 1000 ppm.
Figure 5:
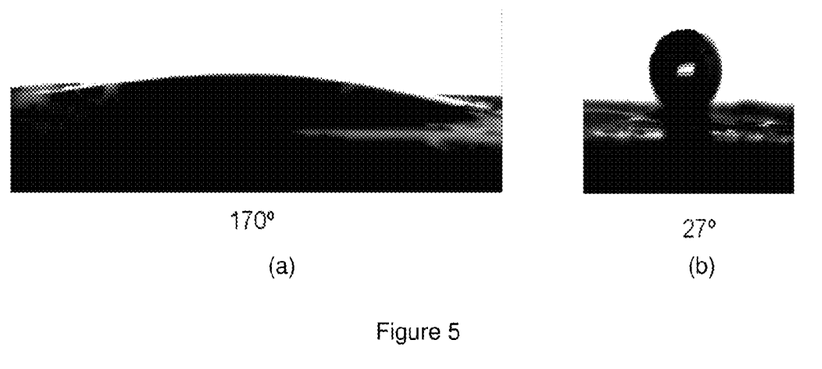
FIG. 5 shows the change in contact angle of a drop of crude oil A added after two hours of being immersed in brine without additive and in additive brine with the chemical product 2 at a concentration of 1000 ppm: (a) the contact angle of oil after 2 hours, (b) the contact angle of oil after 2 hours it has been treated with chemical product 2 (0.1%).

FIGS. 1 and 2 show the oil separating from the rock by the action of chemicals products 1 and 2 respectively at different exposure times, FIGS. 3 and 4 show the contact angles of a drop of oil on the rock two hours after being immersed in the 1.0 brine additive with chemicals products 1, 2 and 3 respectively, at a concentration of 1000 ppm of the chemical.

TABLE 1

Properties of crude oils A and B used in performance tests.

| Propertie | A | B |
|---|---|---|
| Density at 25° C. y 585 mmHg | 0.852 | 0.926 |
| ° API | 36 | 17 |
| Composition (% weight) | | |
| Crystallizable paraffins | 6.13 | 4.59 |
| Saturated hydrocarbon fraction | 54.80 | 5.87 |
| Aromatic hydrocarbon fraction | 23.57 | 41.15 |
| Polar hydrocarbon fraction (resins) | 21.21 | 41.84 |
| Asphaltenes | 0.41 | 11.13 |

Table 4 shows the contact angles obtained at the beginning of the test and by dropping a drop of crude oil after two hours of being immersed in the brine additive rock with chemicals products 1, 2 and 3, these results is tested by changing the wettability favorable oil-wet rock to wet rock by water.

TABLE 2

| Crude oil | Acid number (mgKOH/g) | Basic Number (mgKOH/g) |
|---|---|---|
| A | 0.24 | 0.38 |
| B | 0.24 | 4.04 |

TABLE 3

| Salt | Concentration ppm (mg/L) |
|---|---|
| NaCl | 129,693 |
| $CaCl_2$ | 152,855 |
| $MgCl_2 \cdot 6H_2O$ | 39,1785 |
| $FeSO_4 \cdot 7H_2O$ | 3 |
| $NaHCO_3$ | 1881.2 |

TABLE 4

| Chemical product | Concentration (ppm) | Crude oil | Contact angle |
|---|---|---|---|
| Reference | 0 | A | 170° |
| Reference | 0 | B | 167° |
| 1 | 1000 | A | 30° |
| 1 | 1000 | B | 40° |
| 2 | 1000 | A | 27° |
| 2 | 1000 | B | 35° |
| 3 | 1000 | A | 35° |
| 3 | 1000 | B | 45° |

Example 5

Evaluation of Spontaneous Imbibition Process

The products evaluated were: chemical product 1 and a chemical derivative of the commercial product mixture of alkyl sulfonate sodium, quaternary ammonium salts and betaines.

For this Assessment Amott Cells were Used, the Procedure was as Follows:

1) Small fragments of rock from the well Cantarell 26D, lithology type with limestone, washed continuously at reflux temperature of the following solvents: a) Xylene, b) Chloroform, c) methane and d) Xylene, e) Chloroform, f) Methanol, g) Xylene. The last residue of the washing solvent was colorless and staying analyzed by gas chromatography coupled with mass spectrometry to confirm that is not exist the presence of hydrocarbon. All the washing process was in 8 days.

2) The rock fragments were dried in an oven at a temperature of 100° C. and record the weight after reaching a constant weight.

3) Small fragments of rock were brought into contact with oil from the well dead for 24 hrs. at a temperature of 95° C. and 1500 (psi) in a cell aging, finally fragments were removed and allowed to drip for about three hours until there was no longer observed oil drip, each of the portions of fragments of rock was weighed and was obtained by difference in weight the amount of oil adsorbed on the porous medium.

4) Each of small fragments of rock soaked with oil were placed individually in Amott cells and contacted at room temperature and atmosferic pressure with a) synthetic brine, b) synthetic brine containing 0.2% by weight of the chemical product 1 and c) synthetic brine containing 0.2% by weight of the commercial product derived from the mixture of alkyl sulfonates, and betaine.

5) The rock fluid systems were left in contact at a temperature of 25° C., for 7 days. Cells Amott imbibition type shown in FIG. 6, wherein (A) represents the brine additive to the commercial product derived from alkyl sulfonates, and betaine, (B) brine without chemicals, (C) represents the additive brine with the chemical product 1 and (D) The crude oil recovered.

Figure 6:
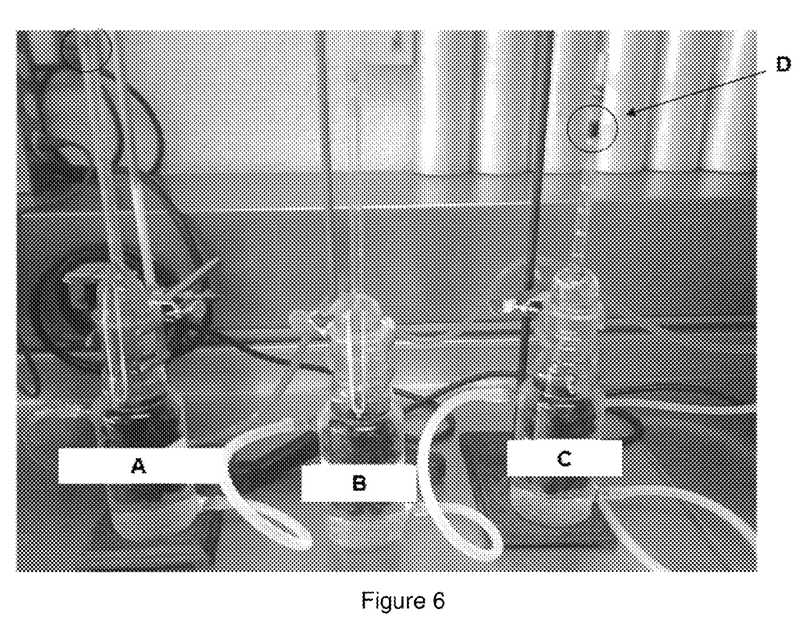
FIG. 6 illustrates the amott cells, where: (A) represents the brine with the commercial product with additives derived from alkyl sulfonates and betaines (B) brine without chemicals, (C) represents the additive brine with chemical product 1, and (D) recovered crude oil.

The results are shown in Table 5 and the equipment used in the experiment in FIG. 6.

The analysis of the results in Table 5 shows that at a temperature of 25° C., the synthetic brine that simulates the characteristics of the connate water is unable to displace the oil that is imbibed by the porous medium and the chemical product 1 is 133% more efficient than the commercial product derived from alkyl sulfonates, and betaine.

Subsequently, at 7 days that the systems were at 25° C., the temperature thereof was increased to 65° C. and left in contact at this temperature for 7 days, at which time the results were obtained which are shown in Table 6.

TABLE 5

| Sample | Day 7 | | |
|---|---|---|---|
| | Initial oil in rock (g) | Oil recovered (g) | % Recovered |
| Brine | 2.13 | 0.0 | 0.0 |
| Chemical product 1 | 1.70 | 0.24 | 14.7% |
| Commercial product derived from alkyl sulfonates and betaine. | 1.74 | 0.11 | 6.3% |

TABLE 6

Oil recovered at temperatura of 65° C.

| Sample | Day 14 | | |
|---|---|---|---|
| | Initial oil in rock (g) | Oil recovered (g) | % Recovered |
| Brine | 2.13 | 0.14 | 0.0 |
| Chemical product 1 | 1.70 | 0.74 | 43.5% |
| Commercial product derived from alkyl sulfonates and betaine. | 1.74 | 0.50 | 28.7% |

The analysis in table 6 shows that at a temperature of 65° C. the synthetic brine was able to recover 6.5% of original oil which was adsorbed by the porous medium and the chemical product 1 is 52% more efficient than the product alkyl sulfonates derived from commercial betaines and, therefore, the chemical product 1 proved to be more efficient than the commercial product in spontaneous imbibition process, when the temperature increases the efficiency of the chemical product 1 increases.

Example 6

Experimental procedure for dual-core displacement. In order to simulate the conditions prevailing in an oil well, took out the evaluation of the chemical product 1 to conditions of high temperature (140° C.) and high pressure (2500 psi).

The procedure is as follows:
1. Cleaning of the rock samples with many solvents and placed in the injection cell.
2. Saturation of the rock samples to initial conditions of the test. First saturated with brine and then 100% oil is injected until the residual water saturation.
  a) Saturation of the rock samples with water or brine: applying a confining pressure of 1500 psi, vacuum is induced within one hour and then proceeds to inject the water from the bottom of the cell until reaching a pressure of 1000 psi stable.
  b) Rock samples saturation with oil: Under these conditions water saturation, the entire system is brought to the temperature and pressure conditions under which the test is carried oil recovery (140° C., 2500 psi). The oil injection rate was 1 ml/hr.
  c) Aging: It is aged for 7 days in system test conditions (140° C., 2500 psi)
3. Home testing improved recovery process: The double displacement process is carried and pressure conditions of constant temperature and under injection of 1 ml/hr.
  a) Injection of brine: To start the process lines are filled with water and injected through the bottom of the cell to a 1 ml/hr. The top measures the amount of oil produced in time.
  b) Injecting gas ($N_2$, $CO_2$, etc.): Gas is injected through the top of the cell to a 1 ml/hr. Measuring the volume of oil is recovered from the bottom of the cell.
  c) The chemical injection: is injected from the bottom of the cell with the chemical added brine (1 ml/hr) and measuring the recovery of oil from the top of the cell. Is injected pore volume injection and suspended for 7 days and the system is isolated so that the chemical action. Restarts the injection and measured the oil produced.

After carrying different kinds of recovery techniques as expansion, water injection, gas injection and nitrogen, the core could be obtained more than 2.8% crude oil through the use of the chemical product 1, which shows its effectiveness even after use other methods of recovery.

Table 7 shows the cumulative recovery with injection of the chemical product 1.

TABLE 7

Recovery volume accumulated over different recovery techniques.

| Gas injection | Cumulative recovery at the end of injection of water (mL) | Cumulative recovery at the end of gas injection (mL) | Cumulative recovery at the end of a chemical product injection (mL) |
|---|---|---|---|
| Nitrogen | 117.06 | 126.46 | N/A |
| Natural gas | 118.78 | 159.55 | 166.49 |

The invention claimed is:

1. A composition of geminal zwitterionic liquid comprising bis-N-alkyl or bis-N-alkenyl or N-cycloalkyl or N-aryl bis-beta aminoacids or its salts thereof with wettability modifying properties, said composition including said geminal zwitterionic liquid in an amount from 5 to 90% by weight, and a solvent in a range of 10 to 95% by weight based on the total weight of the composition, and where said geminal zwitterionic liquid has the formula where:
$R_1$ is a radical represented by —H or —$CH_3$,
$R_2$ is an alkenyl or alkyl chain, or an alkyl or a group;
$R_3$ is a radical represented by —H or and
n and m have values from 1 to 250.

2. The composition in accordance with claim 1, wherein said geminal zwitterionic liquid is included at a concentration of 20 to 50% by weight.

3. The composition in accordance with claim 1, wherein the solvent is included at a concentration preferably of 50 to 80% by weight.

4. The composition in accordance with claim 1, wherein the solvents used are distilled or brine with a high content of divalent ions selected from the group consisting of calcium and magnesium, organic solvents selected from the group consisting of methanol, ethanol, isopropanol and mixtures thereof, xylene, toluene, diesel, gasoline, or mixtures thereof.

5. The composition in accordance with claim 1, wherein the solvents are distilled water, brine with high content of divalent ions, or a mixture of isomers of xylene.

6. A geminal zwitterionic liquid having the following molecular structure:

where:
R$_1$ is a radical represented by —H or —CH$_3$,
R$_2$ is an alkenyl or alkyl chain, or an alkyl or aryl group cycle;
R$_3$ is a radical represented by —H or —CH$_3$; and
n and m can have values from 1 to 250, depending on the molecular weight of poly (other) used.

7. The geminal zwitterionic liquid in accordance with claim 6, wherein R$_1$ and R$_3$ are —H, and R$_2$ is an alkenyl chain represented by —C$_{18}$H$_{35}$, and has the following chemical structure:

Where n = 12

8. A process of obtaining a geminal zwitterionic liquid of claim 6, by the following synthesis route:

comprising three reaction stages:
I. a first phase comprising reacting of formula I, derived from ethylene oxide and propylene oxide or copolymers thereof with two hydroxyl groups, at the terminal ends of the polymer chain, and having an average molecular weight in the range of 100 to 20,000 g/mol; with any of the compounds represented by the letter A: where A is selected from the group consisting of tosyl chloride and mesyl chloride, wherein the reaction is carried out with a molar ratio between the polyglycols of formula I and the compounds of type A of 1:2 to 1:4, with an alkaline base sodium hydroxide, potassium or cesium, using a solvent selected from the group consisting of water, tetrahydrofuran, acetonitrile, and mixtures thereof; for a reaction time of 1 to 8 hours, and at a temperature of 0 to 40° C., to form the compound of formula III;
II. a second stage comprising reacting the compound of formula III via a nucleophilic substitution with a compound of formula IV: where $R_2$ is a linear or branched alkyl or alkylene amine having 1 to 30 carbon atoms, a cycloalkyl or aryl having 5 to 12 carbon atoms, wherein the reaction is carried out with a molar ratio between the compounds of formula III and IV of 1:1.5 to 1:4, in the presence of a solvent selected from the group consisting of acetonitrile, dimethylformamide, dimethylsulfoxide, acetone and short chain alcohols, at a reaction time of 1 to 10 hours, and a temperature of 60 to 100° C., to obtain the secondary amines of formula V; and III. a third reaction step of reacting the secondary amine of formula V with a compound of formula VI: where $R_3$ is acrylic or methacrylic acid, wherein the reaction is carried out with a molar ratio between the compounds of formula V and VI of 1:1.5 to 1:4, the reaction is carried out in the absence or presence of a solvent selected form the group consisting of water, alcohols, toluene, xylene mixtures, o-xylene, m-xylene, p-xylene, kerosene and jet fuel, the reaction time from 1 to 24 hours, the temperature of 40 to 180° C., and pressure from 585 to 760 mmHg, and neutralizing the compounds of formula VII with a base selected from the group consisting of hydroxides, carbonates and bicarbonates of sodium, potassium or cesium.

9. The synthesis process according to claim 8, wherein the polyglycol of formula I has an average molecular weight in the range from 100 to 20,000 g/mol.

10. The synthesis process according to claim 8, wherein the compound used is tosyl chloride.

11. The synthesis process according to claim 8, wherein the molar ratio of the polyglycol of formula I and the compound A is 1:2.2 to 1:2.6.

12. The synthesis process according to claim 8, wherein the alkali base used in the first stage of the second synthetic route is sodium hydroxide.

13. The synthesis process according to claim 8, wherein the operating conditions of the first stage of the second synthetic route have a reaction time of 2 to 5 hours and a temperature of 5 to 40° C.

14. The synthesis process according to claim 8, wherein the alkyl or alkenyl amines of formula IV are linear or branched having 1 to 30 carbon atoms.

15. The synthesis process according to claim 8, wherein $R_2$ of formula IV is an alkyl or alkenyl group having 1 to 30 carbon atoms.

16. The synthesis process according to claim 8, wherein $R_2$ of formula IV is a cycloalkyl or aryl having 5 to 12 carbon atoms.

17. The synthesis process according to claim 8, wherein the molar ratio between the compounds of formula III and IV is 1:1.8 to 1:2.6.

18. The synthesis process according to claim 8, wherein the solvent used in the second stage of the second synthetic route is acetonitrile.

19. The synthesis process according to claim 8, wherein the operating conditions of the second stage of the second synthetic route have a reaction time of 4 to 6 hours and temperatures of 70 to 85° C.

20. The synthesis process according to claim 8, wherein the unsaturated acids of formula VI are acrylic and methacrylic acid.

21. The synthesis process according to claim 8, wherein the molar ratio between the compounds of formula V and VI is 1:1.8 to 1:2.6.

22. The synthesis process according to claim 8, wherein the solvent used in the second reaction step is selected from the group consisting of water, toluene, xylene, o-xylene, m-xylene, p-xylene, kerosene and jet fuel.

23. The synthesis process according to claim 8, wherein the operating conditions of the second reaction step have a reaction time of 1 to 10 hours and temperatures of 80 to 130° C.

24. The synthesis process according to claim 8, wherein the compounds of formula VII are neutralized with bases selected from the group consisting of hydroxides, carbonates, and bicarbonates of sodium, potassium or cesium.

25. A process of enhancing crude oil recovery in a reservoir comprising the step of
introducing a geminal zwitterionic liquid into the reservoir in an amount effective to enhance separation of the crude oil from rock in the reservoir, wherein said geminal ionic liquid has the formula where:
$R_1$ is a radical represented by —H or —$CH_3$,
$R_2$ is an alkenyl or alkyl chain, or an alkyl or aryl group;
$R_3$ is a radical represented by —H or —$CH_3$; and
n and m have values from 1 to 250.

26. The process of claim 25, wherein said crude oil in said reservoir is in the presence of a brine containing a divalent ion selected from the group consisting of calcium, magnesium, barium and strontium, and said rock is selected from the group consisting of limestone, dolomite, sand, quartz and heterogeneous lithologies.

27. The process of claim 26, wherein the salt concentration of said brine is up to 400,000 ppm.

28. The process of claim 26, wherein the divalent ion concentration of said brine is up to 180,000 ppm.

29. The process of claim 25, wherein the temperature in said reservoir is up to 220° C.

30. The process of claim 25, wherein the pressure in said reservoir is up to 4000 psi.

31. The process of claim 25, wherein the geminal zwitterionic liquid is introduced into said reservoir at a concentration of 25 to 40,000 ppm.

32. The process of claim 25, wherein the geminal zwitterionic liquid is introduced into said reservoir at a concentration of 500 to 10,000 ppm.

33. The process of claim 25, wherein the geminal zwitterionic liquid introduced into said reservoir is a composition comprising 5 to 90% by weight of said geminal zwitterionic liquid and 10 to 95% by weight of a solvent.

* * * * *